United States Patent
Honda et al.

(10) Patent No.: US 10,456,150 B2
(45) Date of Patent: Oct. 29, 2019

(54) DISCHARGE DEVICE

(71) Applicant: TERUMO KABUSHIKI KAISHA, Shibuya-ku, Tokyo (JP)

(72) Inventors: Kei Honda, Hadano (JP); Wataru Karino, Atsugi (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 715 days.

(21) Appl. No.: 15/068,715

(22) Filed: Mar. 14, 2016

(65) Prior Publication Data

US 2016/0262776 A1 Sep. 15, 2016

(30) Foreign Application Priority Data

Mar. 13, 2015 (JP) .............................. 2015-051288

(51) Int. Cl.
*A61B 17/22* (2006.01)

(52) U.S. Cl.
CPC .... *A61B 17/22* (2013.01); *A61B 2017/22062* (2013.01); *A61B 2017/22082* (2013.01)

(58) Field of Classification Search
CPC . A61B 17/22; A61B 17/221; A61B 17/22031; A61B 17/12186; A61B 25/0074; A61B 18/02; A61B 18/1815; A61B 17/320758; A61B 18/04; A61M 1/0056; A61M 25/1011; A61M 25/0017; A61M 27/008; A61M 25/0026; A61M 25/1002; A61F 5/44; A61F 5/445; A61F 2/94; A61F 5/0076; A61F 2/04

USPC ........................ 604/921, 916, 96.01, 103.02
See application file for complete search history.

(56) References Cited

U.S. PATENT DOCUMENTS

| | | | | | |
|---|---|---|---|---|---|
| 4,271,839 | A | * | 6/1981 | Fogarty | A61M 25/0119 604/271 |
| 5,332,402 | A | * | 7/1994 | Teitelbaum | A61F 2/2409 623/2.35 |
| 6,485,500 | B1 | * | 11/2002 | Kokish | A61M 25/104 604/101.01 |
| 9,517,080 | B2 | * | 12/2016 | Honda | A61B 17/22 |
| 2003/0229332 | A1 | * | 12/2003 | Intoccia | A61B 17/22 604/508 |
| 2005/0288632 | A1 | * | 12/2005 | Willard | A61M 25/10 604/103.01 |

FOREIGN PATENT DOCUMENTS

JP 2001-512355 A 8/2001
WO WO 98/36694 A1 8/1998

\* cited by examiner

*Primary Examiner* — Manuel A Mendez
(74) *Attorney, Agent, or Firm* — Buchanan Ingersoll & Rooney PC

(57) ABSTRACT

A discharge device and method are disclosed that can discharge a discharge substance with a desired discharge amount at a desired flow rate. A storage unit provided in a discharge device includes a storage space which can store a discharge substance, and a discharge section which can discharge the discharge substance stored in the storage space toward the proximal side of a main body in an axial direction, and is configured to be capable of expanding deformation and contracting deformation in response to introduction and discharge of the discharge substance.

20 Claims, 11 Drawing Sheets

200~~# DISCHARGE DEVICE

CROSS-REFERENCES TO RELATED APPLICATIONS

This application claims priority to Japanese Application No. 2015-051288 filed on Mar. 13, 2015, the entire content of which is incorporated herein by reference.

TECHNICAL FIELD

The present disclosure relates to a discharge device used in order to discharge a discharge substance inside a biological organ.

BACKGROUND DISCUSSION

In the medical field, a discharge device is known which is used in order to discharge a drug solution to be applied to a lesion area inside biological organs (for example, a body cavity such as esophagus, airway, bowel, urinary duct, and other internal organs), in order to discharge a gel-phase substance to be applied in order to protect an inner wall of the biological organ during various treatments, and in order to discharge a cleaning solution for cleaning the biological organ, for example.

The discharge device is configured to guide a discharge substance to flow to a desired site inside a living body through an elongated flexible catheter (shaft). The catheter is formed to have a small outer diameter so that the catheter can be delivered to a relatively thin site in a biological lumen or the like. A discharge substance circulating lumen (flow path) formed inside the catheter is formed to have a small sectional area in accordance with the outer diameter of the catheter.

Incidentally, the discharge device is widely used in order to discharge various discharge substances inside the living body. One of various uses is to remove foreign substances present inside the biological organ. For example, the discharge device can be used in order to discharge a fluid such as a liquid and the like inside the biological organ. In this manner, various treatments for causing the fluid to wash the foreign substances away are performed so as to discharge foreign substances out from the living body or so as to move the foreign substances to a desired position inside the living body. In addition, removal target foreign substances include calculus fragments that are formed by fragmenting a urinary calculus when urolithiasis is treated (refer to JP-T-2001-512355).

As described above, since the catheter itself is formed to have a small diameter and thus has restrictions on a sectional area of the lumen included in the discharge device, the catheter cannot be designed larger. Therefore, it can be difficult to increase a discharge amount or a flow rate of the discharge substance that is discharged through the lumen of the catheter, thereby causing a problem in that the discharge amount or the flow rate required for removing the foreign substances may not be sufficiently obtained. In addition, when the discharge device is used for another use except for removing the foreign substances, for example, when a medicine is intended to be discharged, it can be difficult to secure a desired discharge amount. Consequently, there can occur a problem in that an effect of the medicine (medicinal effect) may not be sufficiently achieved.

SUMMARY

A discharge device is disclosed that can discharge a discharge substance with a desired discharge amount at a desired flow rate.

According to the present disclosure, a discharge device is disclosed, which includes an elongated flexible main body that has a lumen which extends in an axial direction and through which a fluid discharge substance to be discharged inside a biological organ can flow, and a communication hole which communicates with the lumen, a storage unit that includes a storage space which communicates with the lumen through the communication hole and which can store the discharge substance, and a discharge section which can discharge the discharge substance stored in the storage space toward a proximal side of the main body in the axial direction, and that is capable of expanding deformation and contracting deformation in response to introduction and discharge of the discharge substance, and a hub that is provided in a proximal portion of the main body, and that can be connected to and separated from a supply device for supplying the discharge substance.

According to the discharge device of the present disclosure, the inside of a storage space can temporarily store a predetermined amount of discharge substances which are supplied to a storage unit through a lumen of a main body, and the stored discharge substances can be discharged all at once from the inside of the storage space. In accordance with an exemplary embodiment, a discharge amount and a discharging flow rate of the discharge substance can be adjusted in accordance with the amount stored in the storage space. Accordingly, regardless of a sectional area size of the lumen through which the discharge substance flows, discharging can be realized with a desired discharge amount at a desired flow rate.

A method is disclosed for discharging a discharge substance inside a biological organ, the method comprising: inserting a discharge device into a living body, the discharge device including: an elongated flexible main body that has a lumen which extends in an axial direction and through which a fluid discharge substance to be discharged inside the biological organ can flow, and a communication hole which communicates with the lumen; a storage unit that includes a storage space which communicates with the lumen through the communication hole and which can store the discharge substance, and a discharge section which can discharge the discharge substance stored in the storage space toward a proximal side of the main body in the axial direction, and that is capable of expanding deformation and contracting deformation in response to introduction and discharge of the discharge substance; and a hub that is provided in a proximal portion of the main body, and that can be connected to and separated from a supply device for supplying the discharge substance.

A method is disclosed of treating urolithiasis, the method comprising: forming calculus fragments by fragmenting a removal target urinary calculus; delivering a storage unit of a discharge device to a distal side of a living body from the calculus fragments; expanding and deforming the storage unit by supplying a predetermined amount of the discharge substance to the storage unit; and moving the calculus fragments toward a proximal side of the living body by causing the discharge substance stored in the storage unit to flow out from the storage unit.

BRIEF DESCRIPTION OF THE DRAWINGS

FIGS. 2A and 2B are views illustrating the discharge device according to the first embodiment, wherein FIG. 2A is a perspective view illustrating the discharge device, and FIG. 2B is a sectional view taken along line IIB-IIB illustrated in FIG. 2A.

FIGS. 7A and 7B are views illustrating a discharge device according to a second embodiment, wherein FIG. 7A is a perspective view illustrating the discharge device, and FIG. 7B is a sectional view taken along line VIIB-VIIB illustrated in FIG. 7A.

FIGS. 8A and 8B are views illustrating modification examples of the storage unit, wherein FIG. 8A is a perspective view illustrating Modification Example 1 of the storage unit, and FIG. 8B is a perspective view illustrating Modification Example 2 of the storage unit.

FIGS. 10A and 10B are views illustrating modification examples of the storage unit, wherein FIG. 10A is a perspective view illustrating Modification Example 4 of the storage unit, and FIG. 10B is a perspective view illustrating Modification Example 5 of the storage unit.

FIGS. 11A and 11B are views illustrating modification examples of the storage unit, wherein FIG. 11A is a perspective view illustrating Modification Example 6 of the storage unit, and FIG. 11B is a perspective view illustrating Modification Example 7 of the storage unit.

DETAILED DESCRIPTION

Figure 1:
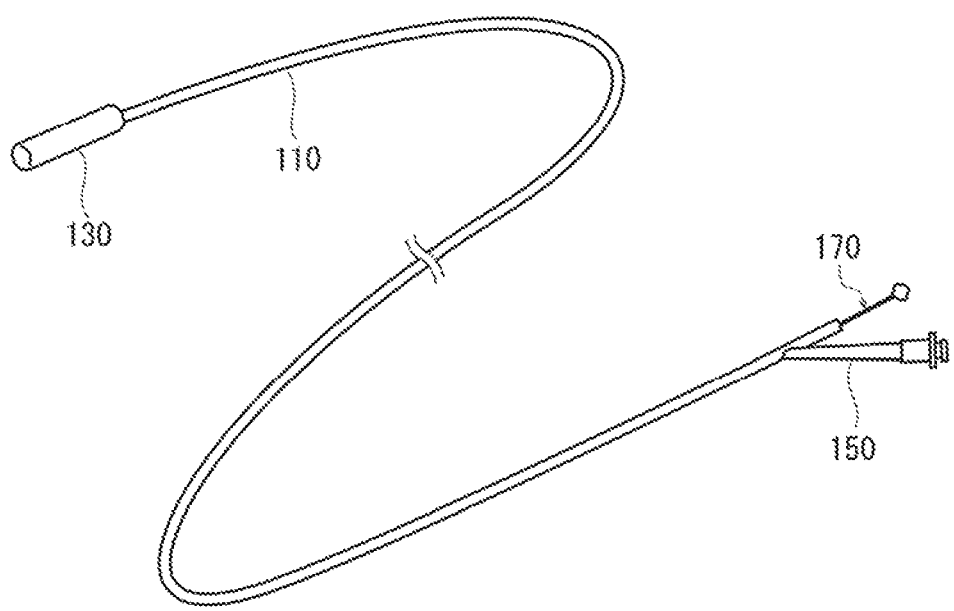
FIG. 1 is a perspective view illustrating a discharge device according to a first embodiment.

Hereinafter, embodiments of the present disclosure will be described with reference to the respective drawings. In some cases, dimensional proportions in the drawings may be exaggerated and different from actual proportions for convenience of description.

Figure 3A:
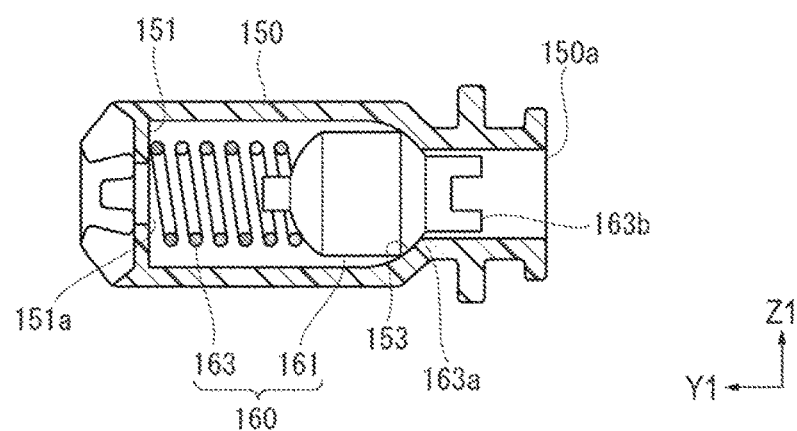
FIGS. 3A and 3B are views illustrating an operation of a reverse flow preventing section included in the discharge device.
Figure 3B:
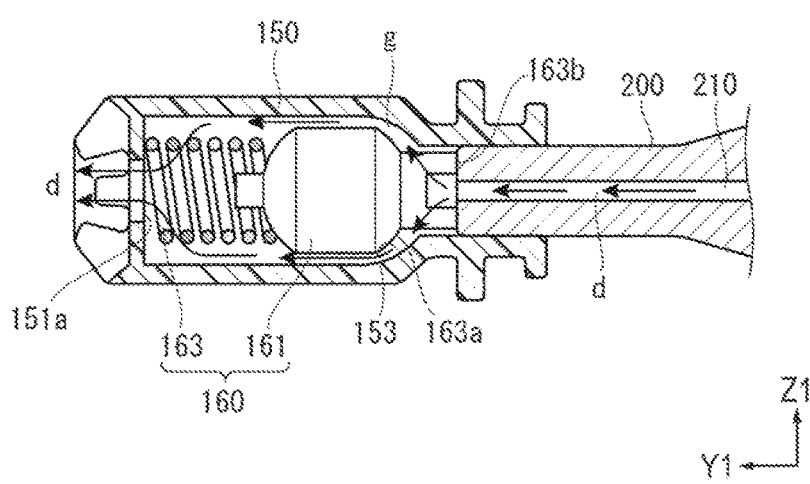
Figure 4A:
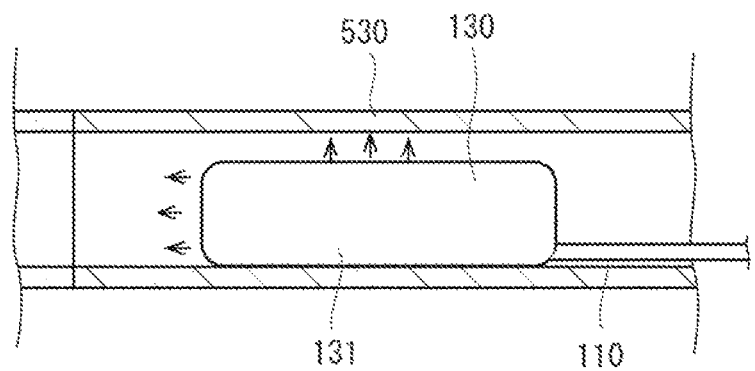
FIGS. 4A to 4C are views respectively illustrating a state before and after a storage unit included the discharge device is expanded and deformed.
Figure 4B:
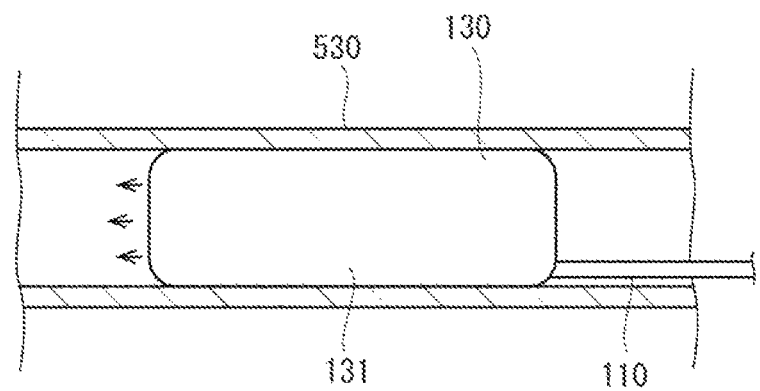
Figure 4C:
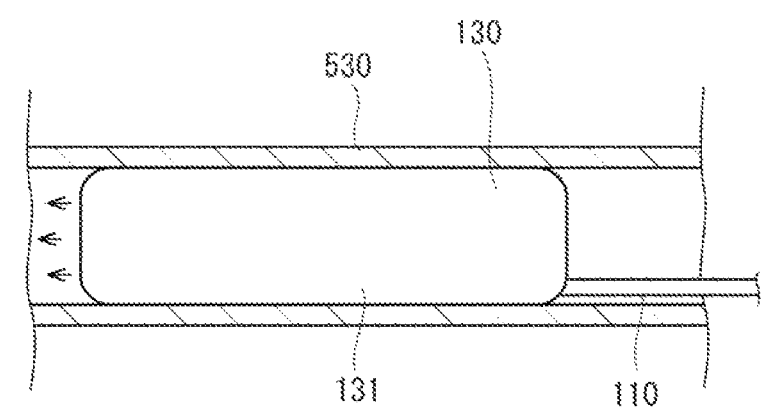
Figure 5:
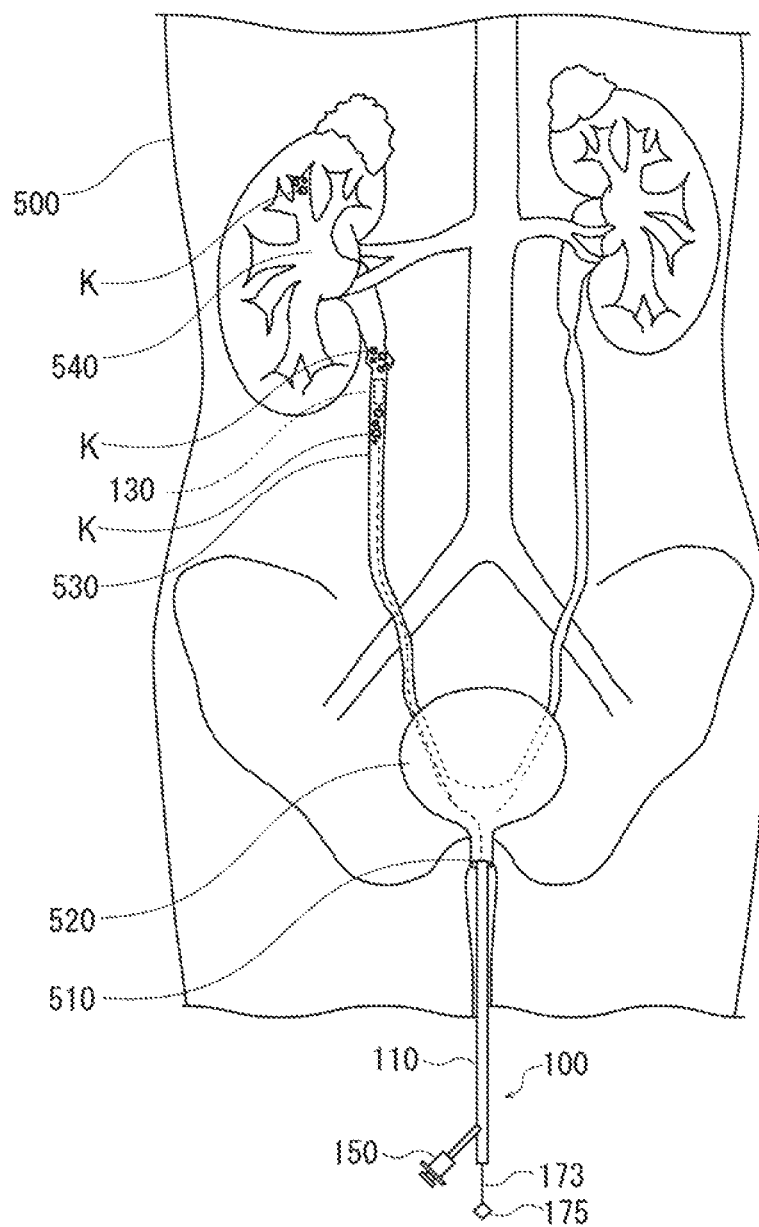
FIG. 5 is a view schematically illustrating a patient (living body) who is a target for treatment performed by using a medical device.
Figure 6A:
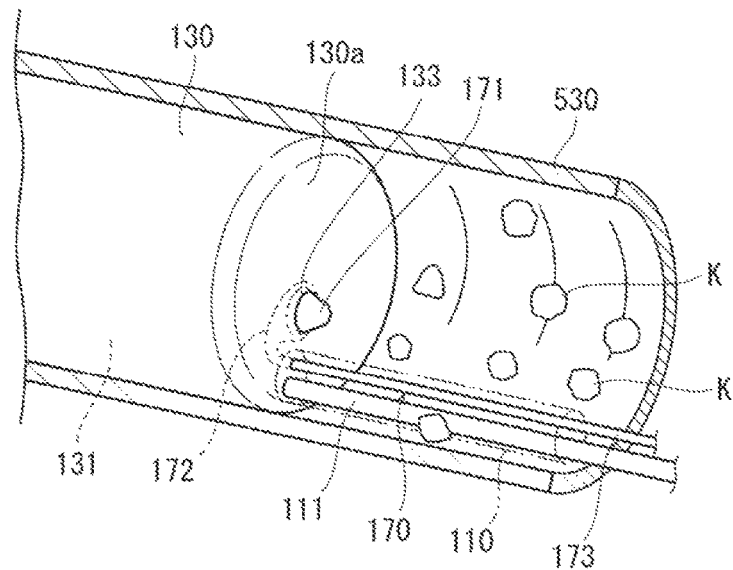
FIGS. 6A and 6B are perspective sectional views for describing an operation of the discharge device according to the first embodiment.
Figure 6B:
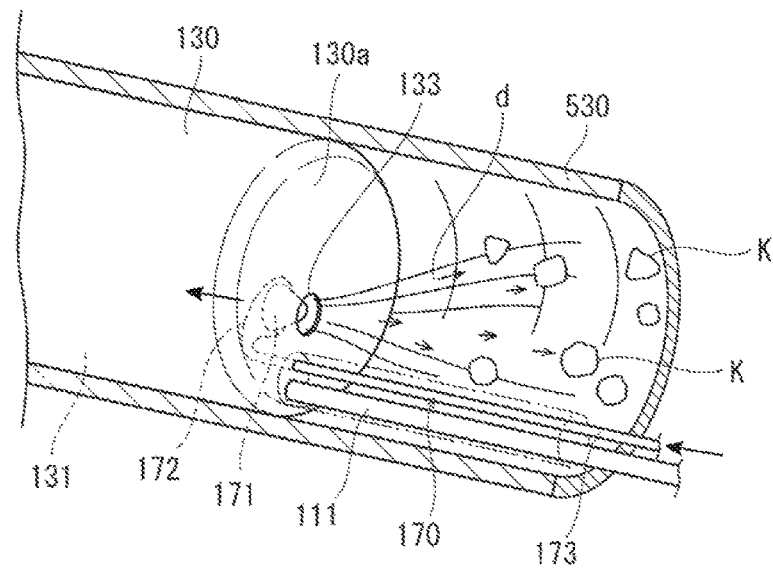

FIGS. 1 to 4C are views illustrating a configuration of each unit of a discharge device according to a first embodiment. FIG. 5 is a view schematically illustrating a living body (patient) which is a target for treatment performed by using the discharge device, and FIGS. 6A and 6B are views for describing a use example and an operation of the discharge device.

In the description of the embodiment, the discharge device according to the embodiment will be described by citing an example in which the discharge device is applied to treatment for urolithiasis.

First, the urolithiasis and a method of treating the urolithiasis will be described with reference to FIG. 5.

The urinary calculus is present in a urinary tract such as a renal pelvis and renal calyx 540 of the kidney, a urinary duct 530, a bladder 520, and a urethra 510. The urinary calculus is broadly classified into an upper urinary calculus present in the kidney or the urinary duct 530, and a lower urinary calculus present between the bladder 520 and an outlet (external urethral orifice) of the urethra 510.

The urolithiasis is a disease in which a calculus formed in the kidney (renal pelvis and renal calyx 540) is moved to the urinary duct 530 so that the calculus damages an inner surface of the urinary duct 530, thereby causing a pain or bloody urine, or in which the calculus occludes the urinary duct 530 and results in a transient hydronephrosis state, thereby causing a patient to feel a severe pain (colicky pain) from the waist back to the flank. As a method of relieving or treating the symptoms of the urolithiasis, to remove the calculus is regarded as effective means. In recent years, an active removing method has been used in order to actively remove the calculus through a surgical treatment.

The active removing method can include extracorporeal shock wave lithotripsy (ESWL), transurethral lithotripsy (TUL or URS), and percutaneous nephrolithotomy (PNL or PCNL). In addition, the TUL can include r-TUL (or r-URS) which employs a rigid pyeloscope (hereinafter, referred to as a "rigid scope"), and f-TUL (or f-URS) which employs a flexible pyeloscope (hereinafter, referred to as a "flexible scope").

In the TUL described above, a device (for example, a laser lithotripsy device) which fragments the calculus by using a rigid scope or a flexible scope is caused to reach the calculus inside the urinary duct 530 or inside the renal pelvis and renal calyx 540 through the urethra 510, the bladder 520, and the urinary duct 530, thereby enabling the device to directly fragment the calculus inside the living body. Therefore, by adopting the TUL, it is possible to suppress the damage to the urinary duct 530, and the kidney, and thus a highly efficient stone free rate can be achieved compared to a case of adopting ESWL or PNL.

However, the calculus fragments which are finely fragmented are less likely to be removed by using basket forceps or the like without leaving any remainder. In addition, even if the calculus fragments are removed by using the basket forceps, a period of time for manual skills is considerably prolonged. On the other hand, a method of removing the calculus fragments by a water current using perfusion water of an endoscope (a flexible scope or a rigid scope) is also conceivable. However, the urinary duct has a narrow lumen, and extends inside the body in a meandering manner. Moreover, a patient sleeps while lying facing upward at an almost horizontal angle during the surgery. Therefore, it cannot be expected that the calculus is naturally discharged by using the perfusion water.

In accordance with an exemplary embodiment, a discharge device 100 according to the present embodiment relates to a medical device, which can efficiently remove the calculus fragments present inside the urinary duct 530 or inside the kidney. In the description below, the urinary calculus and the fragments thereof are referred to as calculus fragments K.

The discharge device 100 will be described.

Figure 2A:
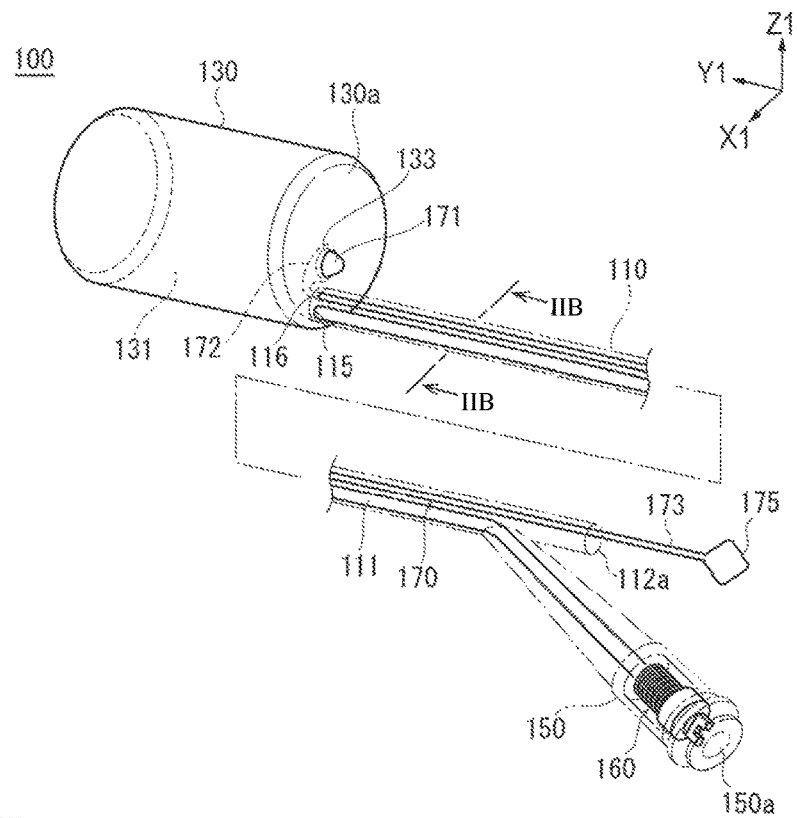

As illustrated in FIGS. 1 and 2A, the discharge device 100 can include an elongated main body 110 that can be introduced into biological organs (the urinary duct 530, and the renal pelvis and renal calyx 540), a storage unit 130 that is disposed at a distal portion of the main body 110, and a hub 150 that is disposed at a proximal portion of the main body 110. In order to illustrate each internal structure of the main body 110 and the hub 150, the contour line of the main body 110 or the hub 150 is illustrated by using a two-dot chain line in some drawings such as FIG. 2A.

In the description herein, a side of the discharge device 100 (side on which the storage unit 130 is disposed) to be inserted into the living body is referred to as a distal side, and an operation hand side of the discharge device 100 (side on which the hub 150 is disposed) is referred to as a proximal side. In addition, in the drawings, an X1 axis indicates a depth direction of the discharge device 100, an Y1 axis indicates an axial direction (extending direction) of the discharge device 100, and a Z1 axis indicates a height direction of the discharge device 100. The distal portion and the distal side mean a predetermined range from a distal end portion to the proximal side, and do not mean only the distal end portion. Similarly, the proximal portion and the proximal side mean a predetermined range from a proximal end portion to the distal side, and do not mean only the proximal end portion.

Figure 2B:
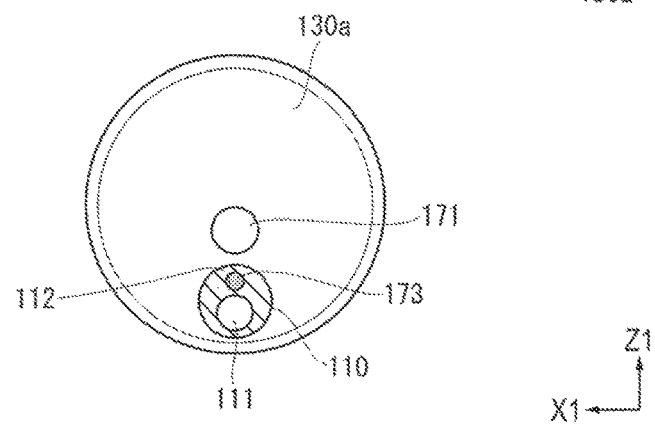

As illustrated in FIGS. 2A and 2B, a lumen 111 which extends in the axial direction and through which a fluid discharge substance to be discharged inside the biological organ flows, and a communication hole 115 which communicates with the lumen 111 are formed in the main body 110.

The main body 110 is disposed so that a distal end surface faces a proximal surface 130a of the storage unit 130, and two lumens 111 and 112 communicate with a storage space 131 in a liquid-tight and air-tight manner through two communication holes 115 and 116 formed on the distal end surface of the main body 110.

The storage unit 130 can include the storage space 131 which communicates with the lumen 111 through the communication hole 115 and which can store the discharge substance, and a discharge section 133 which can discharge the discharge substance stored in the storage space 131 toward the proximal side of the main body 110 in the axial direction. The storage unit 130 is configured to be capable of expanding deformation and contracting deformation in response to the introduction and the discharge of the discharge substance. In each drawing, the discharge of the discharge substance from the storage unit 130 is illustrated by using an arrow d (for example, refer to FIGS. 6A and 6B).

The hub 150 has a configuration in which the hub can be connected to and separated from a supply device (not illustrated) for supplying the discharge substance to the discharge device 100. As the supply device, for example, an indeflator or a syringe, which are known in the medical field can be used.

The discharge substance is supplied into the hub 150 by the supply device and then, flows into the lumen 111 of the main body 110 through the hub 150. The discharge substance that has passed through the lumen 111 flows into the storage space 131 of the storage unit 130 through the communication hole 115 communicating with the lumen 111. The storage unit 130 is expanded and deformed due to an increase in the internal pressure in response to the discharge substance flowing into the storage space 131. In addition, if the discharge substance stored (held) in the storage space 131 is discharged by the discharge section 133 (refer to FIG. 6B), the storage unit 130 is contracted and deformed due to a decrease in the internal pressure in response to the discharge.

As illustrated in FIG. 6B, the discharge section 133 is configured to include a hole portion (through-hole) that allows communication between the inside and the outside of the storage space 131. The discharge section 133 is formed on the proximal surface 130a of the storage unit 130. In addition, the discharge device 100 can include a switching section 170 that can switch between open and closed states of the discharge section 133 configured to include the hole portion.

In a case where the discharge is performed by using the discharge device 100, an operation is performed by using the switching section 170 in order to switch the discharge section 133 from a closed state to an open state.

As illustrated in FIG. 2A, the switching section 170 has a blocking portion 171 that blocks the discharge section 133, and an extension portion 173 that extends from the blocking portion 171 toward the proximal side, and that helps enable the blocking portion 171 to unblock the discharge section 133 by using a hand operation. In addition, as illustrated in FIGS. 2A and 2B, the main body 110 is provided with an insertion lumen 112 into which the extension portion 173 of the switching section 170 is inserted, a proximal opening portion 112a which is formed on the proximal side of the insertion lumen 112 and from which a portion (proximal portion) of the extension portion 173 is extracted, and a communication hole 116 which allows communication between the inside of the storage space 131 and the insertion lumen 112.

A user operates the extension portion 173 extracted from the main body 110 with his or her finger so as to carry out work for opening the discharge section 133 by using the switching section 170.

As illustrated in FIG. 6A, the blocking portion 171 is fitted into the hole portion configuring the discharge section 133, thereby sealing the hole portion and maintaining a closed state of the discharge section 133. In addition, as illustrated in FIG. 6B, the extension portion 173 of the switching section 170 is operated so as to move the blocking portion 171 from the hole portion. In this manner, it is possible to start discharging the discharge substance.

As illustrated in FIG. 2A, the blocking portion 171 is configured to include a protruding portion formed in a substantially conical shape which is tapered toward the proximal side from a bending portion 172 that is formed by partially bending the distal side of the extension portion toward the proximal side of the main body 110.

As illustrated in FIG. 6A, in a state where the blocking portion 171 is fitted into the discharge section 133, the discharge section 133 is blocked (sealed) and thus the discharge of the discharge substance is restricted. Then, as illustrated in FIG. 6B, if the blocking portion 171 is moved toward the distal side of the main body 110 so as to cause the blocking portion 171 to retreat from the discharge section 133, the discharge section 133 is brought into the open state, and the discharge substance starts to be discharged. For example, the work for opening the blocking portion 171 is carried out by pressing the extension portion 173 forward to the distal side through a hand operation.

As illustrated in FIG. 2A, a gripping portion 175 for facilitating gripping of the switching section 170 when a user operates the switching section 170 is provided in the proximal portion of the extension portion 173. For example, the gripping portion 175 can be configured to include a flat plate-shaped member as illustrated in the drawing. For example, although a shape of the gripping portion 175 can be formed in a rectangular shape, or a circular shape, the shape is not particularly limited.

As illustrated in FIG. 2A, the storage unit 130 is configured to include a container which can store a predetermined discharge substance inside the storage space 131 formed therein. For example, the storage unit 130 can be configured to include a flexible material, which enables expanding deformation and contracting deformation in response to a change in the internal pressure.

For example, the storage unit 130 can be configured to include the same material as that of a balloon used for a balloon catheter in the medical field. Examples of the material include polyolefin such as polyethylene, polypropylene, ethylene-propylene copolymer, polyester such as polyethylene terephthalate, a thermoplastic resin such as polyvinyl chloride, ethylene-vinyl acetate copolymer, crosslinked ethylene-vinyl acetate copolymer, polyurethane, polyamide elastomer, polystyrene elastomer, silicone rubber, or latex rubber.

In a case where the storage unit 130 is configured to include a relatively high flexible material, the blocking portion 171 is not firmly fitted into the discharge section 133, thereby causing a possibility of degraded sealing performance. For example, in order to prevent the sealing performance from being degraded, the periphery of the discharge section 133 can be configured to be harder than other portions or can be configured to be thicker than other portions.

FIG. 2A illustrates an enlarged state of the storage unit 130. When being expanded and deformed, the storage unit 130 is configured to have a substantially cylindrical shape having a predetermined length in the axial direction. However, an expanded and deformed shape is not particularly limited, and thus can be appropriately changed.

For example, the storage unit 130 can be configured such that an expanding deformation amount in the axial direction in response to the introduction of the discharge substance further increases than an expanding deformation amount in a radially outward direction, after pressure inside the storage space 131 reaches predetermined pressure. FIGS. 4A to 4C illustrate an example of a change in an expanded shape of the storage unit 130 configured in this way.

As illustrated in FIG. 4A, in an initial stage of the expanding deformation, the storage unit 130 expands at substantially the same expansion rate in the radial direction (vertical direction in the drawing) and in the axial direction (horizontal direction in the drawing). As illustrated in FIGS. 4B and 4C, after the outer surface of the storage unit 130 comes into contact with the inner wall of the urinary duct 530, the storage unit 130 continuously expands in the axial direction at a predetermined expansion rate, whereas a radially expanded amount resulting from an increase in internal pressure considerably decreases.

In order to prevent damage or the like to the biological organs (urinary duct 530), it is not preferable to set the maximum expansion diameter of the storage unit 130 to a dimension which is far beyond the diameter of the lumen of the biological organ. Therefore, it is preferable to impose restrictions on the radially expanded and deformed amount to some extent. On the other hand, when a treatment is performed so as to wash the calculus fragments K away by using the discharge substance, it can be preferable to adopt a configuration in which a larger amount of discharge substances can be stored therein. The expanded and deformed amounts of the storage unit 130 in the radial direction and the axial direction are adjusted as described above. In this manner, while the biological organ is prevented from being damaged, the amount of storage-available discharge substances can be increased.

For example, as a method of adjusting the expanded and deformed amount of the storage unit 130 in the radial direction, the following methods can be adopted such as an adjusting method of using a type of materials, an adjusting method of using a suppressing tool for suppressing expanding deformation (for example, a rubber band, which is harder than the storage unit 130), an adjusting method of using the wall thickness, a method of causing a material to partially contain particles for changing compliant characteristics, an adjusting method of using an expansion rate employed when a material configuring the storage unit 130 is molded.

When the discharge device 100 is configured to function as a medical device for removing the urinary calculus (calculus fragments K), the storage unit 130 can be configured so as to be capable of storing the discharge substance of 0.3 ml to 2.8 ml to the maximum, for example. In addition, the length of the storage unit 130 in the axial direction at the time of the maximum expansion can be formed to be 50 mm to 100 mm, for example. The outer diameter of the storage unit 130 at the time of the maximum expansion can be formed to be 3.0 mm to 6.0 mm, for example.

The storage unit 130 can include a function of partially blocking the biological organs (the urinary duct 530 and the renal pelvis and renal calyx 540) in addition to a function of temporarily storing a predetermined amount of the discharge substance.

As illustrated in FIG. 6A, the storage unit 130 expands radially outward so as to spread out the lumen of the biological organ, and partially blocks the biological organ by bringing the outer peripheral surface in contact with the inner wall of the biological organ. In a state where the biological organ is partially blocked in this way, if the discharge substance stored in the storage unit 130 starts to be discharged, the discharge substance flows out from the discharge section 133 formed on the proximal surface 130a of the storage unit 130 toward the proximal side of the main body 110 in the axial direction. The discharge substance that has flowed out is blocked so as not to flow from the storage unit 130 toward the distal side of the storage unit 130. Therefore, the discharge substance mainly flows toward the further proximal side from the storage unit 130. As described, the flowing direction of the discharge substance can be directed toward the further proximal side from the storage unit 130. Therefore, in a state of being contracted to some extent before starting the discharge, the storage unit 130 is disposed on the further distal side (rear side of the biological organ) from the calculus fragments K, which are removal targets. In this manner, the calculus fragments K can be efficiently removed or moved by using the discharge substance.

As a fluid discharge substance used in order to remove the urinary calculus (the calculus fragments K), liquid, gas, and a fluid mixture thereof can be used, for example. As an example, it is possible to use a physiological salt solution, helium gas, $CO_2$ gas, $O_2$ gas, and a fluid obtained by appropriately combining those materials. In addition, the "fluid discharge substance" according to the present embodiment means that the entire discharge substance forms a flow. For example, as the discharge substance, a powder, a granular material, a gel-phase substance, and a foam-like substance can be used.

As illustrated in FIG. 2A, the communication hole 116 which allows communication between the insertion lumen 112 of the main body 110 and the inside of the storage space 131 is formed to have substantially the same diameter as the outer diameter of the extension portion 173 of the switching section 170 so that the communication hole does not interrupt the moving operation of the switching section 170 when the discharge section 133 is open, and so that the discharge substance does not leak from the communication hole 116 in a state where the switching section 170 is inserted. A known sealing member such as an O-ring and the like can be attached to the communication hole 116 in order to more reliably prevent the discharge substance from leaking from the communication hole 116.

For example, the blocking portion 171 can be configured to automatically block the discharge section 133 (close the discharge section 133) by utilizing the increase in the internal pressure of the storage space 131. As illustrated in FIG. 2A, if the blocking portion 171 and the discharge section 133 are disposed to have a positional relationship of facing each other, the blocking portion 171 is moved toward the discharge section 133 by the increased internal pressure of the storage space 131. Therefore, the blocking portion 171 can be fitted into the discharge section 133 without performing a hand operation on the blocking portion 171. If the diameter of the communication hole 116 which is formed on the proximal surface 130a of the storage unit 130 is set to be substantially the same as the outer diameter of the extension portion 173 of the switching section 170, the switching section 170 can be prevented from being inadvertently rotated. Accordingly, a state can be maintained where the blocking portion 171 and the discharge section 133 face each other. Therefore, and it is possible to relatively easily achieve automation of a blocking operation using the blocking portion 171.

The material configuring the switching section 170 (the blocking portion 171, the bending portion 172, and the extension portion 173) is not particularly limited as long as an operating force (pulling force) during the hand operation can be transferred to the distal side. However, for example, as the material, a thermoplastic resin such as vinyl chloride, polyurethane, polyethylene, polypropylene, polystyrene, or a copolymer thereof, nylon, PET, a thermosetting resin such as rubber, silicone elastomer, a fibrous material such as silk thread, cotton thread, and a cellulose fiber, a metal material such as SUS wire, copper wire, titanium wire, nitinol wire, or a material obtained by appropriately combining these materials can be used.

As illustrated in FIGS. 3A and 3B, a hub 150 is provided with a reverse flow preventing section 160 that prevents a reverse flow of the discharge substance to be supplied to the storage unit 130.

The reverse flow preventing section 160 can include a valve body 161, and a biasing member (spring) 163 that applies a biasing force to the valve body 161. A distal portion of the biasing member 163 is fixed to an inner wall 151 of the distal portion of the hub 150. As illustrated in FIG. 3A, when a supply unit (tube) 200 of the supply device that supplies the discharge substance is not connected to the hub 150, the valve body 161 is biased by the biasing member 163 so as to be pressed against an inclined wall 153 of the hub 150. A sealing portion is formed on a portion at which a base portion 163a of the valve body 161 and the inclined wall 153 are in contact with each other. Therefore, the discharge substance can be prevented from reversely flowing toward the proximal side of the valve body 161, that is, toward a proximal opening portion 150a of the hub 150.

As illustrated in FIG. 3B, when the supply unit 200 of the supply device is interlocked with the proximal opening portion 150a of the hub 150, the valve body 161 is pressed against the distal side by the supply unit 200. In this manner, a flow path (gap g) through which the discharge substance can flow is formed between the base portion 163a of the valve body 161 and the inclined wall 153. In this state, the discharge substance is supplied to the hub 150 through a lumen 210 of the supply unit 200, the discharge substance flows into the lumen 111 of the main body 110 attached to the distal end of the hub 150 via the inside of the hub 150 and a distal opening portion 151a of the hub 150. When the supply unit 200 is detached from the hub 150, the valve body 161 is moved to a position illustrated in FIG. 3A due to the biasing force applied to the valve body 161 by the biasing member 163. In this manner, a sealing portion is formed on a portion at which the base portion 163a of the valve body 161 and the inclined wall 153 are in contact with each other.

A configuration of the reverse flow preventing section 160 is not particularly limited as long as the reverse flow preventing section 160 prevents the discharge substance from reversely flowing from the discharge device 100 toward the supply device side in a state where the discharge substance is supplied into the storage unit 130. In addition, a position for installing the reverse flow preventing section 160 is not limited to the inside of the hub 150. For example, the reverse flow preventing section 160 can also be disposed inside the main body 110, or in the vicinity of the communication hole 115 that allows the communication between the lumen 111 of the main body 110 and the storage unit 130.

Next, a use example and an operation of the discharge device 100 will be described.

Here, with regard to a patient 500 who suffers from the urolithiasis, a treatment example for the patient 500 will be described in which a calculus is present in a region corresponding to a lower urinary duct of the urinary duct 530 where a rigid scope can reach, and a calculus is present in a region corresponding to an upper urinary duct of the urinary duct 530 where the rigid scope is less likely to reach but a flexible scope can reach. In this case of disease, the calculus in the lower urinary duct is first removed and then, the calculus in the upper urinary duct is removed. FIG. 5 schematically illustrates a situation when the calculus of the upper urinary duct is removed after the calculus of the lower urinary duct is removed.

First, for the patient 500 who suffers the urolithiasis, a guide wire that is widely known in the medical field is introduced to the urinary duct 530 or the renal pelvis and renal calyx 540 through the urethra 510 and the bladder 520 by using a cystoscope (flexible scope or rigid scope) that is generally used in the urinary system.

Next, the rigid scope is inserted so as to observe the inner wall of the urinary duct 530 or the calculus inside the urinary duct 530. In this case, the calculus can be removed by using a known calculus-extracting device such as basket forceps in combination with the rigid scope.

Then, the urinary calculus which is relatively large and less likely to be removed is fragmented by using a lithotripter, for example, such as a holmum YAG laser or in combination with the rigid scope so as to form the calculus fragments K.

Next, as illustrated in FIG. 5, the main body 110 of the discharge device 100 is introduced into the living body. Although not illustrated, for example, the main body 110 of the discharge device 100 can be inserted via a forceps channel (lumen) of the rigid scope.

Then, as illustrated in FIG. 6A, the storage unit 130 of the discharge device 100 is disposed on the further distal side (rear side of the urinary duct 530) from the calculus fragments K, which are the removal targets. Thereafter, the discharge substance is supplied to the storage unit 130 through the lumen 111 of the main body 110. After it is confirmed that the urinary duct 530 is partially blocked by the storage unit 130 after the storage unit 130 is expanded and deformed, the rigid scope is pulled out to the inside of the bladder 520 or to the outside of the body. As illustrated in FIG. 6B, the discharge section 133 is open so as to cause the discharge substance to flow out. The calculus fragments K, which are located on the further proximal side from the storage unit 130 are washed away toward the bladder 520 by the discharge substance.

Next, a guide wire is used in order to insert a urethral access sheath into the urinary duct 530 or the renal pelvis and renal calyx 540 through the urethra 510 and the bladder 520. The urethral access sheath is introduced after the calculus fragments K are removed from the urinary duct 530 by using the discharge device 100. Accordingly, there is no possibility of clogging of the calculus fragments K between the urethral access sheath and the inner wall of the urinary duct 530. Therefore, the urinary duct 530 can be suitably prevented from being damaged, perforated, or fractured, for example.

Next, the flexible scope is inserted through the ureteral access sheath so as to observe the calculus fragments K. The guide wire may be appropriately extracted. Since the calculus fragments K are already removed, even when the flexible scope is inserted, the urinary duct 530 can be prevented from being damaged due to the calculus fragments K.

In a case where the calculus is a relatively large and less likely to pass through the ureteral access sheath, the calculus is fragmented by using a lithotripter, for example, such as a holmum YAG laser in combination with the flexible scope so as to form the calculus fragments K. After the calculus fragments K are formed, the calculus fragments K are removed by using the discharge device 100 again.

As a series of treatments described above is appropriately and repeatedly performed, the removal of the urinary calculus is completed. In the method of treating the urolithiasis according to the embodiment, the "treatment of removing the urinary calculus and the calculus fragments K" can include a treatment of directly extracting the calculus from the site (the renal pelvis and renal calyx 540 or the urinary duct 530) where the calculi are generated inside the living body to the outside from the living body, and a treatment (repositioning) of moving the calculus from the site where the calculi are generated inside the living body to another site. In addition, the "repositioning" can include, for example, a movement between different renal pelvises or different renal calices 540 and a movement from the renal pelvis and renal calyx 540 and the urinary duct 530 to the bladder 520.

The method of treating the urolithiasis described above can include (i) forming the calculus fragments by fragmenting the removal target urinary calculus, (ii) delivering the storage unit of the discharge device to the further rear side (distal side) of the living body from the calculus fragments, (iii) expanding and deforming the storage unit by supplying a predetermined amount of the discharge substance to the storage unit, and (iv) moving the calculus fragments toward the peripheral side (proximal side) of the living body by causing the discharge substance stored in the storage unit to flow out from the storage unit.

In accordance with an exemplary embodiment, storage space 131 can temporarily store a predetermined amount of the discharge substances which are supplied to the storage unit 130 through the lumen 111 of the main body 110, and the stored discharge substances can be discharged all at once from the storage space 131. In accordance with an exemplary embodiment, a discharge amount and a discharging flow rate of the discharge substance can be adjusted in accordance with the amount stored in the storage space 131. Accordingly, regardless of a sectional area size of the lumen 111 through which the discharge substance flows, discharging can be realized with a desired discharge amount at a desired flow rate, and the calculus fragments K can be efficiently removed.

In addition, the discharge section 133 is configured to include a hole portion that allows communication between the inside and the outside of the storage space 131, and the discharge device 100 can include the switching section 170 that can switch between open and closed states of the discharge section 133. Therefore, it is possible to cause the discharge section 133 to start discharging the discharge substance by the simple operation of opening the discharge section 133 by using the switching section 170.

In addition, the switching section 170 has the blocking portion 171 that blocks the hole portion configuring the discharge section 133, and the extension portion 173 that extends from the blocking portion 171 toward the proximal side, and that enables the blocking portion 171 to unblock the hole portion by using a hand operation. Therefore, discharging by the discharge section 133 can be realized by the simple work for operating the extension portion 173 by a hand operation.

In addition, the blocking portion 171 is configured to be fitted into the hole portion configuring the discharge section 133 and to seal the hole portion, the extension portion 173 is operated so as to move the blocking portion 171 from the hole portion. In this manner, discharging the discharge substance can be started. Therefore, discharging of the discharge substance can be realized by the simple work for moving the blocking portion 171 by a hand operation.

In addition, the storage unit 130 can be configured such that an expanding deformation amount in the axial direction in response to the introduction of the discharge substance further increases than an expanding deformation amount in a radially outward direction, after pressure inside the storage space 131 reaches predetermined pressure. Therefore, while the tubular tissue of the urinary duct 530 can be prevented from being damaged at the time of the expanding deformation, it is possible to increase the amount of storage-available discharge substances.

In addition, the discharge device 100 is configured to function as a medical device for removing the urinary calculus and/or the calculus fragments K present in the urinary duct 530 or the renal pelvis and renal calyx 540, and the discharge substance is a liquid. Therefore, a medical device capable of efficiently removing the urinary calculus or the calculus fragments K can be provided.

Next, a discharge device according to a second embodiment of the present disclosure will be described. In the description of the second embodiment, the descriptions regarding the same members as those described above, similar configurations, and the like are appropriately omitted.

Figure 7A:
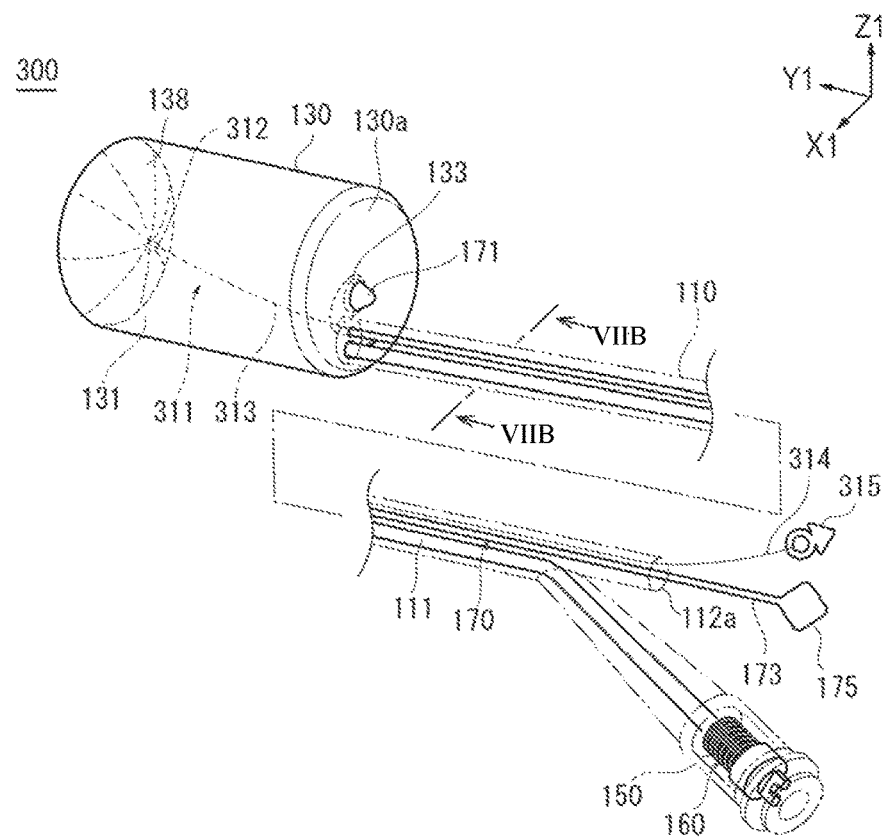
Figure 7B:
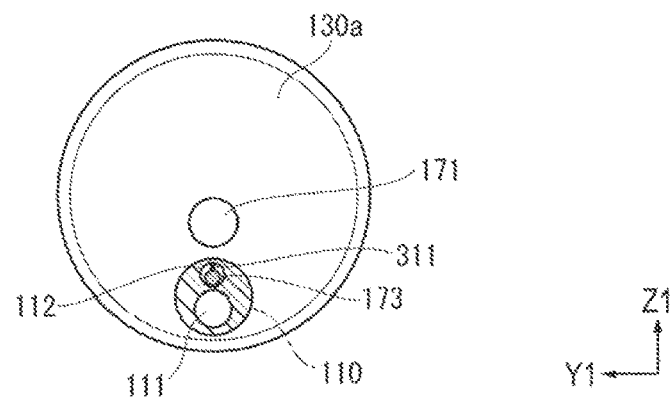

FIGS. 7A and 7B illustrate a discharge device 300 according to the second embodiment. FIG. 7A is a perspective view of the discharge device 300, and FIG. 7B is a cross-sectional view taken along line VIIB-VIIB in FIG. 7A.

The discharge device 300 is provided with a moving member 311 that moves an inner surface 138 of the distal portion of the storage unit 130 toward the proximal side.

The moving member 311 is configured to include an elongated member that has a fixed portion 312 which is fixed to the inner surface 138 of the distal portion of the storage unit 130, and an extension portion 313 which extends from the fixed portion 312 toward the proximal side. The extension portion 313 is inserted through the insertion lumen 112 formed in the main body 110. In addition, a proximal portion 314 of the extension portion 313 is extracted to the outside from the proximal opening portion 112a of the main body 110.

A gripping portion 315 for facilitating gripping of the moving member 311 when a user operates the moving member 311 is provided in the proximal portion 314 of the extension portion 313. For example, as illustrated in FIG. 7A, the gripping portion 315 is configured to have an arrow shape indicating a moving direction so that the user can visually confirm the moving direction (pulling direction) of the moving member 311 when the user operates the moving member 311.

The extension portion 313 of the moving member 311 can be configured to include a thin member having relatively high durability such as metal wire or piano wire, for example. The fixation between the moving member 311 and the storage unit 130 is performed by a known method such as fusion, bonding or the like.

When the proximal portion 314 of the extension portion 313 is pulled by a hand operation, the moving member 311 moves the inner surface 138 of the distal portion of the storage unit 130 toward the proximal side. When the storage unit 130 discharges the discharge substance, if the inner surface 138 of the distal portion of the storage unit 130 is moved toward the proximal side, the force of the discharge substance discharged from the discharge section 133 is increased. As a result, it is possible to increase the discharge amount of the discharge substance to be discharged per unit time, and thus the calculus fragments K can be further efficiently removed.

As in a storage unit 440 or the like illustrated in a modification example described below (refer to FIGS. 10A and B), an operation of opening the discharge section 133 that is performed by moving a blocking portion 441 toward the proximal side along the axial direction by a certain distance can be configured such that, by connecting or the like the moving member 311 to the blocking portion 441 to be integrated, an operation of opening the discharge section 133 and an operation of moving the inner surface 138 of the distal portion of the storage unit 130 toward the proximal side by using the moving member 311 are simultaneously performed with a common operation.

Next, modification examples of the storage unit will be described. In the description of each modification example, the descriptions regarding the same members as those described above, similar configurations, and the like are appropriately omitted. In addition, in the description of each modification example, although main parts of the storage unit are only illustrated, the configuration and the like which are not particularly described can adopt the same configuration as that of each embodiment described above.

Figure 8A:
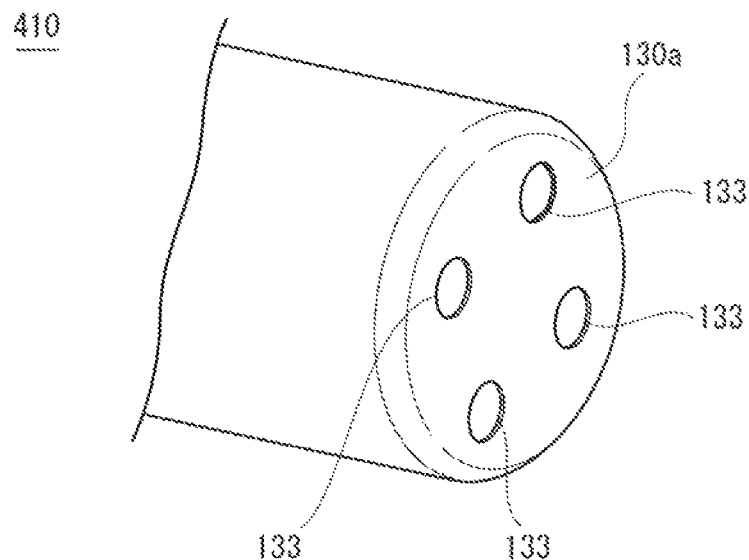

FIG. 8A illustrates main parts of a storage unit 410 according to Modification Example 1.

The discharge section 133 is disposed at multiple different locations in the circumferential direction on the proximal surface 130a of the storage unit 410. By disposing the discharge sections 133 in this manner, it is possible to increase the discharge amount and also it is possible to discharge the discharge substance along the circumferential direction of the inner wall of the urinary duct 530. Therefore, the calculus fragments K can be further efficiently removed. As illustrated in FIG. 8A, by disposing the discharge sections 133 on the proximal surface 130a of the storage unit 410 at uniform intervals in the circumferential direction, it is possible to uniformly discharge the discharge substance along the circumferential direction of the inner wall of the urinary duct 530, and the removal efficiency of the calculus fragments K can be further improved.

Figure 8B:
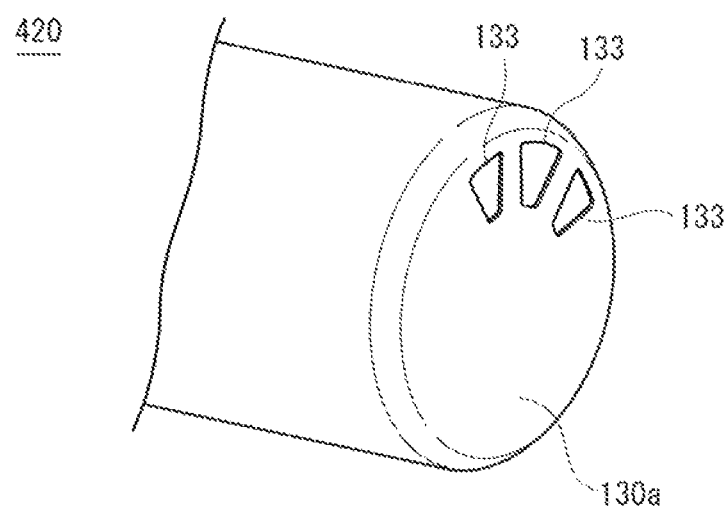

FIG. 8B illustrates main parts of a storage unit 420 according to Modification Example 2.

The shape of the discharge section 133 is not limited to a circular shape, and, as illustrated in the drawing, the discharge section 133 can be formed to have a fan shape, for example. In addition, the discharge section 133 may be formed to have a shape other than the fan shape, such as a rectangular shape, or an elliptical shape. When multiple discharge sections 133 are provided, the discharge sections 133 may have different shapes from each other. In addition, the discharge section 133 may be formed at any part of the proximal surface 130a of the storage unit 420. For example, as illustrated in the drawing, the discharge section 133 can be formed only on the upper side of the proximal surface 130a. The calculus fragments K are deposited on the main body 110 or in a gap between the main body 110 and the urinary duct 530 due to the influence of the gravity. In such a case, by using the discharge device in which the multiple discharge sections 133 are formed only on the upper side of the proximal surface 130a, the discharge substance is discharged toward the calculus fragments K and thus the calculus fragments K float to be washed away. Therefore, the removal efficiency of the calculus fragments K can be further improved.

As in Modification Examples 1 and 2 described above, when multiple discharge sections 133 are formed in one storage unit, if the above-described switching sections 170 is arranged at the same number of locations as the number of the discharge sections 133, the main body 110 is caused to increase in diameter due to increased installation in the lumen 111. In addition, the configuration of the apparatus becomes complicated. In such a case, for example, it can be preferable to provide switching sections (having configurations described in Modification Examples 3, 4, 6, 7 and the like described below) which can be provided without being inserted through the lumen 111 of the main body 110, to the storage unit.

Figure 9A:
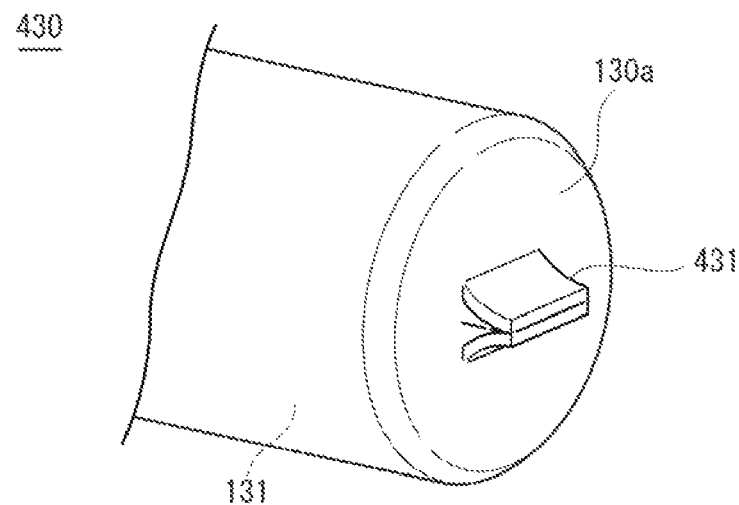
FIGS. 9A and 9B are perspective views illustrating Modification Example 3 of the storage unit.
Figure 9B:
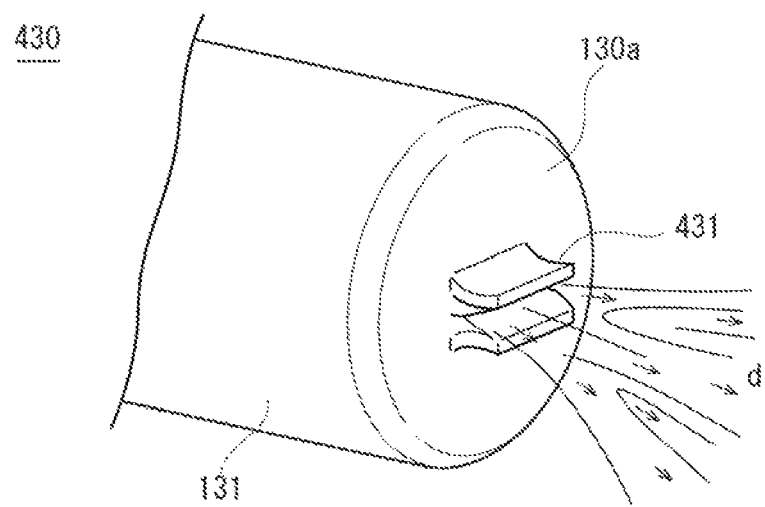

FIGS. 9A and 9B illustrate main parts of a storage unit 430 according to Modification Example 3.

The storage unit 430 is provided with a switching valve 431 that is opened or closed according to the increase or decrease of the pressure in the storage space 131, and switches between the start and the stoppage of the discharge of the discharge substance. In the storage unit 430, since it is possible to automatically switch the start and the stoppage of the discharge according to the amount of the discharge substance stored in the storage space 131, it is possible to save labor for the discharging operation. As the switching valve 431, for example, a duckbill valve or the like which is widely used as a check valve in general can be used. As an example of a switching mechanism of the start and the stoppage of the discharge, the discharge substance is continuously supplied to the storage space 131, and thus the internal pressure of the storage space 131 becomes higher than the upper limit pressure value of the duckbill valve. At this time, two valves of the duckbill valve, which are provided to be pressed against each other are opened, and thus the discharge substance in the storage space 131 is discharged to obtain a discharge-starting state. The two valves of the duckbill valve, which are opened once remain in the open state due to the force of the discharge substance being discharged, while a predetermined amount of the discharge substance is discharged. Thereafter, the two valves of the duckbill valve are pressed against each other again, and thus the switching valve 431 becomes in a closed state to obtain a discharge-stopping state.

Figure 10A:
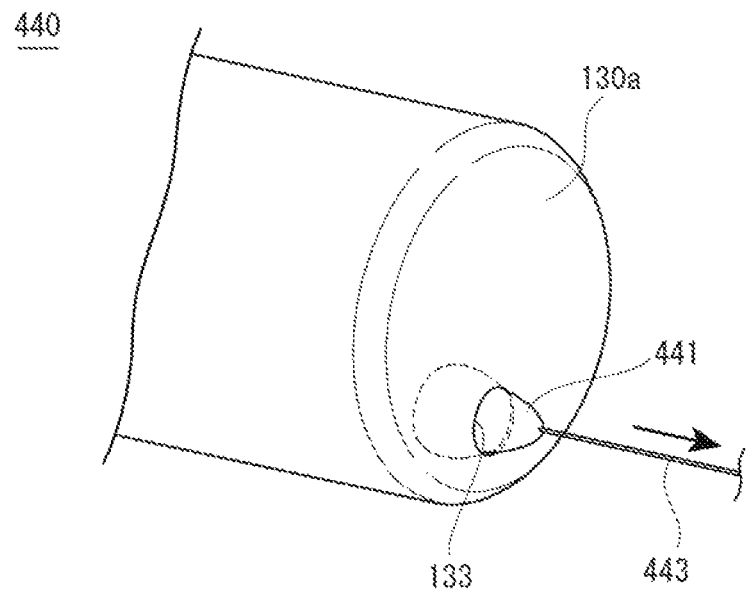

FIG. 10A illustrates main parts of the storage unit 440 according to Modification Example 4.

The storage unit 440 can include a switching section that is configured to include the blocking portion 441 which is separated from the discharge section 133 in accordance with a pulling operation toward the proximal side so as to start discharging the discharge substance, and a string-shaped elongated member 443 that extends from the blocking portion 441 toward the proximal side.

The storage unit 440 is configured to include a flexible material. Therefore, when the blocking portion 441 is pulled, the blocking portion 441 expands the discharge section 133 so as to be easily separated. In addition, since the blocking portion 441 is configured to include an elastic material, the blocking portion 441 is easily separated from the discharge section 133. Since the elongated member 443 is configured to include a string-shaped thin member, the elongated member 443 can be extracted to the outside from the living body through the urinary duct 530 without the insertion of the lumen 111 of the main body 110. In addition, with such a configuration, the blocking portion 441 is firmly fitted into the discharge section 133, and therefore the sealing performance of the storage unit 440 can be improved.

Figure 10B:
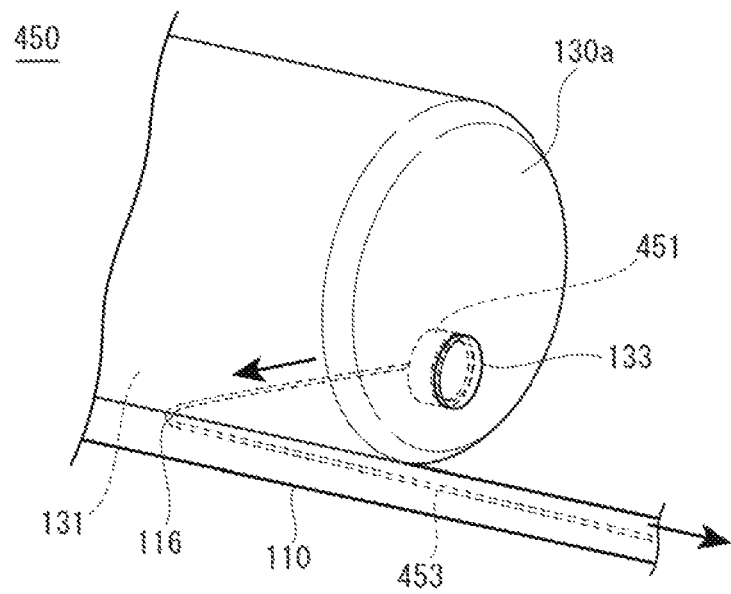

FIG. 10B illustrates main parts of a storage unit 450 according to Modification Example 5.

The storage unit 450 can include a switching section that is configured such that a blocking portion 451 is pulled into the storage space 131 from the discharge section 133 by using a string-shaped elongated member 453 which is caught by the communication hole 116 communicating with the lumen 111 of the main body 110.

Since the elongated member 453 caught by the communication hole 116 forms a fulcrum for pulling the blocking portion 451 into the storage space 131, the discharge section 133 can be opened by moving the blocking portion 451 by an operation of pulling the elongated member 453 toward the proximal side with a hand operation. As illustrated in the present modification example, the disposition of the main body 110 can be appropriately changed as long as the main body 110 is capable of supplying the discharge substance to the storage unit 130.

Figure 11A:
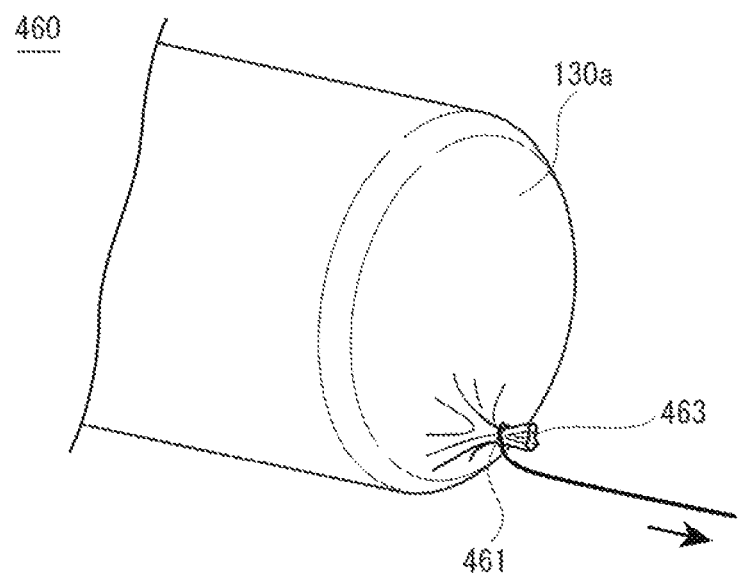

FIG. 11A illustrates main parts of a storage unit 460 according to Modification Example 6.

The storage unit 460 is configured to include a saclike member, and is provided with a discharge section 463 as an opening portion (hole portion) that opens the proximal surface 130a of the storage unit 460. The switching section is configured to include a string-shaped elongated member 461 that forms a knot so as to maintain the discharge section 463 to be in a closed state. It is possible to start discharging from the discharge section 463 by untying the knot of the elongated member 461. Since the elongated member 461 is configured to include a string-shaped thin member, the elongated member 461 can be extracted to the outside from the living body through the urinary duct 530 without the insertion of the lumen 111 of the main body 110.

Figure 11B:
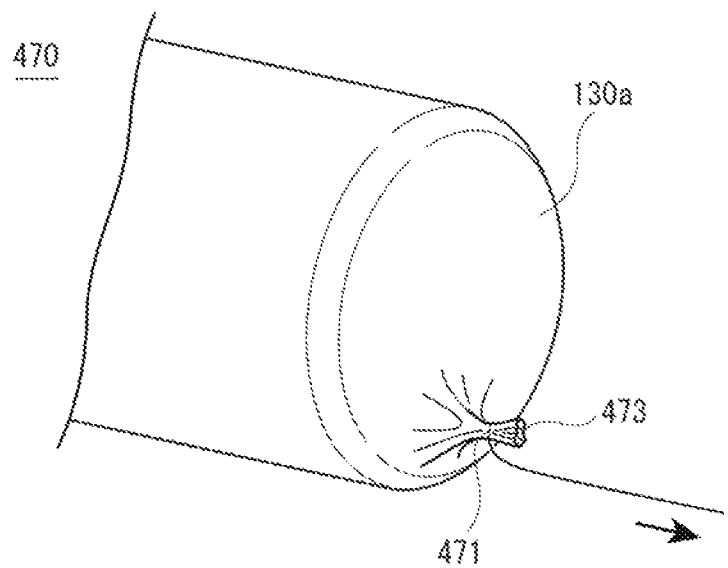

FIG. 11B illustrates main parts of a storage unit 470 according to Modification Example 7.

The storage unit 470 is configured to include a saclike member, and is provided with a discharge section 473 as an opening portion (hole portion) that opens the proximal surface 130a of the storage unit 470. The switching section is configured to include a string-shaped elongated member 471 that sutures (tacking) a part of the storage unit 470 so as to maintain the discharge section 463 to be in a closed state. It is possible to start discharging from the discharge section 473 by untying the suture of the elongated member 471. Since the elongated member 471 is configured to include a string-shaped thin member, the elongated member 471 can be extracted to the outside from the living body through the urinary duct 530 without the insertion of the lumen 111 of the main body 110.

As another modification example, for example, when the discharging starts, a hole portion may be formed to a storage unit by using a sharp member such as wire or a needle without using a member such as the switching section. In a case of using such a configuration, for example, it can be preferable to provide a thin site, which can be easily perforated, or a fragile site which can be easily broken.

As above, although the medical elongated member and the medical instruments according to the present disclosure are described with reference to multiple embodiments and modification examples, the present disclosure is not limited to only the configurations described in the embodiments, and can be appropriately changed based on the description of the claims.

For example, the discharge device according to the present disclosure is not limited to be used for the purpose described in the embodiments, and can be widely applied to a device or the like that is used in order to remove various foreign substances present in the biological organ (for example, a body cavity such as esophagus, airway, bowel, pancreatic duct, bile duct, and ear) other than the kidney and the urinary duct, to discharge a medicine into the biological organ or discharge a gel-phase substance to be used for the purpose of protecting the biological organ or of the embolus, for example.

In addition, the configuration described in each of the embodiments and the modification examples can be appropriately combined with the discharge device or the storage unit according to other embodiments or other modification examples unless the function thereof is damaged.

The detailed description above describes to a discharge device used in order to discharge a discharge substance inside a biological organ. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A discharge device comprising:
   an elongated flexible main body having a lumen which extends in an axial direction and configured to receive a fluid discharge substance to be discharged inside a biological organ, and a communication hole which communicates with the lumen;
   a storage unit that includes a storage space which communicates with the lumen through the communication hole and configured to store the discharge substance, and a discharge section on a proximal surface of the storage unit, the discharge section configured to discharge the discharge substance stored in the storage space toward a proximal side of the main body in the axial direction, and wherein the storage unit is configured to expand and contract in response to introduction and discharge of the discharge substance, the storage unit having a substantially cylindrical shape having a predetermined length in an axial direction when being expanded; and
   a hub that is provided in a proximal portion of the main body, and wherein the hub is configured to be connected to and separated from a supply device for supplying the discharge substance.

2. The discharge device according to claim 1,
   wherein the discharge section is configured to include a hole portion which allows communication between the inside of the storage space and an outside of the storage space, and wherein the discharge device further comprises a switching section configured to switch between open and closed states of the discharge section.

3. The discharge device according to claim 2, wherein the switching section has a blocking portion configured to block the hole portion, and an extension portion which extends from the blocking portion toward the proximal side, and which enables the blocking portion to unblock the hole portion by using a hand operation.

4. The discharge device according to claim 3, wherein the blocking portion is configured to be fitted into the hole portion and configured to seal the hole portion, and
wherein the discharge substance starts to be discharged by operating the extension portion and moving the blocking portion from the hole portion.

5. The discharge device according to claim 1, wherein in the storage unit, an expanding deformation amount in the axial direction in response to the introduction of the discharge substance further increases than an expanding deformation amount in a radially outward direction, after pressure inside the storage space reaches a predetermined pressure.

6. The discharge device according to claim 1, comprising:
a moving member configured to move an inner surface of a distal portion of the storage unit toward the proximal side.

7. The discharge device according to claim 1, comprising:
a switching valve configured to be opened and closed in response to an increase and a decrease in the pressure inside the storage space, and wherein the switching valve is configured to switch the discharge section to start discharging and to stop discharging the discharge substance.

8. The discharge device according to claim 1, wherein the discharge section is disposed at multiple different locations in a circumferential direction on the proximal surface of the storage unit.

9. The discharge device according to claim 1, wherein the discharge device is configured to function as a medical device for removing a urinary calculus and/or calculus fragments present inside the biological organ, and
wherein the discharge device is configured to discharge a liquid as the discharge substance.

10. A method for discharge a discharge substance inside a biological organ, the method comprising:
inserting a discharge device into a living body, the discharge device including:
an elongated flexible main body having a lumen which extends in an axial direction and configured to receive a fluid discharge substance to be discharged inside a biological organ, and a communication hole which communicates with the lumen;
a storage unit that includes a storage space which communicates with the lumen through the communication hole and configured to store the discharge substance, and a discharge section on a proximal surface of the cylindrical storage unit, the discharge section configured to discharge the discharge substance stored in the storage space toward a proximal side of the main body in the axial direction, and wherein the storage unit is configured to expand and contract in response to introduction and discharge of the discharge substance, the storage unit having a substantially cylindrical shape having a predetermined length in an axial direction when being expanded; and
a hub that is provided in a proximal portion of the main body, and wherein the hub is configured to be connected to and separated from a supply device for supplying the discharge substance;
injecting the discharge substance through the lumen of the elongated flexible main body into the storage space of the storage unit; and
discharging the discharge substance from the storage space of the storage unit inside the biological organ.

11. The method according to claim 10, wherein the discharge section is configured to include a hole portion which allows communication between the inside of the storage space and an outside of the storage space, and wherein the discharge device further comprises a switching section, the method comprising:
switching between open and closed states of the discharge section using the switching section.

12. The method according to claim 11, wherein the switching section has a blocking portion, and an extension portion which extends from the blocking portion toward the proximal side, and which enables the blocking portion to unblock the hole portion by using a hand operation, the method comprising:
blocking the hole portion with the blocking portion; and
enabling the blocking portion to unblock the hole portion using the hand operation.

13. The method according to claim 12, comprising:
fitting the blocking portion into the hole portion and sealing the hole portion with the blocking portion; and
start discharging the discharge substance by operating the extension portion and moving the blocking portion from the hole portion.

14. The method according to claim 10, wherein in the storage unit, an expanding deformation amount in the axial direction in response to the introduction of the discharge substance further increases than an expanding deformation amount in a radially outward direction, after pressure inside the storage space reaches a predetermined pressure.

15. The method according to claim 10, comprising:
moving an inner surface of a distal portion of the storage unit toward the proximal side with a moving member.

16. The method according to claim 10, wherein the discharge devices includes a switching valve configured to be opened and closed in response to an increase and a decrease in the pressure inside the storage space, the method comprising:
start discharging and stop discharging the discharge substance with the switch value.

17. The method according to claim 10, comprising:
disposing the discharge section at multiple different locations in a circumferential direction on the proximal surface of the storage unit.

18. The method according to claim 10, wherein the discharge device is configured to function as a medical device for removing a urinary calculus and/or calculus fragments present inside the biological organ, the method comprising:
discharging a liquid as the discharge substance from the discharge device.

19. The method according to claim 10, further comprising:
delivering the storage unit of the discharge device to a distal side of the living body from fragments;

expanding and deforming the storage unit by supplying a predetermined amount of the discharge substance to the storage unit; and moving the fragments toward a proximal side of the living body by causing the discharge substance stored in the storage unit to flow out from the storage unit.

20. A method of treating urolithiasis, the method comprising:

forming calculus fragments by fragmenting a removal target urinary calculus;

delivering a storage unit of a discharge device to a distal side of a living body from the calculus fragments, the storage unit having a discharge section on a proximal surface of the cylindrical storage unit;

expanding and deforming contracting the storage unit by supplying a predetermined amount of the discharge substance to the storage unit, the storage unit having a substantially cylindrical shape having a predetermined length in an axial direction when being expanded; and moving the calculus fragments toward a proximal side of the living body by causing the discharge substance stored in the storage unit to flow out from the storage unit through the discharge section.

* * * * *